United States Patent
Melamed et al.

(10) Patent No.: US 11,860,262 B2
(45) Date of Patent: *Jan. 2, 2024

(54) SYSTEM AND METHODS FOR THREE DIMENSIONAL MODELING OF AN OBJECT USING A RADIO FREQUENCY DEVICE

(71) Applicant: VAYYAR IMAGING LTD, Yehud (IL)

(72) Inventors: Raviv Melamed, Nes Ziona (IL); Damian Hoffman, Tzur Yitzhak (IL); Jonathan Rosenfeld, Ramat hasharon (IL); Ronen Tur, Binyamina (IL)

(73) Assignee: VAYYAR IMAGING LTD, Yehud (IL)

( * ) Notice: Subject to any disclaimer, the term of this patent is extended or adjusted under 35 U.S.C. 154(b) by 66 days.

This patent is subject to a terminal disclaimer.

(21) Appl. No.: 17/403,301

(22) Filed: Aug. 16, 2021

(65) Prior Publication Data

US 2021/0373140 A1    Dec. 2, 2021

Related U.S. Application Data

(63) Continuation of application No. 16/871,397, filed on May 11, 2020, now Pat. No. 11,092,684, which is a
(Continued)

(51) Int. Cl.
  *G01S 13/00* (2006.01)
  *G01B 15/04* (2006.01)
(Continued)

(52) U.S. Cl.
  CPC .......... *G01S 13/003* (2013.01); *G01B 15/04* (2013.01); *G01N 22/00* (2013.01); *G01S 13/862* (2013.01);
(Continued)

(58) Field of Classification Search
  CPC .... G01S 13/887; G01S 13/003; G01S 13/862; G01S 13/89; G01S 13/90; G01B 15/04;
(Continued)

(56) References Cited

U.S. PATENT DOCUMENTS 2,735,070 A    2/1956 Riblet
4,010,715 A    3/1977 Robar et al.
(Continued)

FOREIGN PATENT DOCUMENTS

EP    1845364 A2    10/2007
WO    2014/064425 A2    5/2014
WO    2014/080360 A2    5/2014

OTHER PUBLICATIONS

R. Streich et al., "Accurate imaging of multicomponent GPR data based on exact radiation patterns," IEEE Transactions on Geoscience and Remote Sensing, vol. 45, 93-103 (2007).
(Continued)

*Primary Examiner* — Bernarr E Gregory
(74) *Attorney, Agent, or Firm* — Browdy and Neimark, PLLC

(57) ABSTRACT

A system for generating a three dimension (3D) imaging of an object, the system comprising: an electromagnetic transducer array such as an RF (radio-frequency) antenna array surrounding the object said array comprising: a plurality of electromagnetic transducers; a transmitter unit for applying RF signals to said electromagnetic transducer array; and a receiver unit for receiving a plurality of RF signals affected by said object from said electromagnetic transducers array; a Radio Frequency Signals Measurement Unit (RFSMU) configured to receive and measure said plurality of plurality of affected RF signals and provide RF data of the object; and at least one processing unit, configured to process said RF data to identify the dielectric properties of said object and construct a 3D image of said object.

15 Claims, 7 Drawing Sheets

Related U.S. Application Data continuation of application No. 15/569,827, filed as application No. PCT/IL2016/050479 on May 5, 2016, now Pat. No. 10,690,760.

(60) Provisional application No. 62/157,161, filed on May 5, 2015.

(51) Int. Cl.

| | |
|---|---|
| *G01N 22/00* | (2006.01) |
| *G01S 13/86* | (2006.01) |
| *G01S 13/89* | (2006.01) |
| *G06T 7/50* | (2017.01) |
| *G06T 17/00* | (2006.01) |
| *A61B 5/0507* | (2021.01) |
| *A61B 8/00* | (2006.01) |
| *G01S 13/90* | (2006.01) |
| *H01Q 1/42* | (2006.01) |
| *H01Q 5/48* | (2015.01) |
| *H01Q 5/55* | (2015.01) |
| *H01Q 9/04* | (2006.01) |
| *H01Q 9/28* | (2006.01) |
| *H01Q 13/10* | (2006.01) |
| *H04B 7/0413* | (2017.01) |

(52) U.S. Cl.
CPC .............. *G01S 13/89* (2013.01); *G06T 7/50* (2017.01); *G06T 17/00* (2013.01); *A61B 5/0507* (2013.01); *A61B 8/4416* (2013.01); *G01S 13/90* (2013.01); *H01Q 1/422* (2013.01); *H01Q 5/48* (2015.01); *H01Q 5/55* (2015.01); *H01Q 9/0407* (2013.01); *H01Q 9/285* (2013.01); *H01Q 13/10* (2013.01); *H04B 7/0413* (2013.01)

(58) Field of Classification Search
CPC .......... G01N 22/00; G06T 7/50; G06T 17/00; A61B 5/0507; A61B 8/4416; H01Q 1/422; H01Q 5/48; H01Q 5/55; H01Q 9/0407; H01Q 9/285; H01Q 13/10; H04B 7/0413
See application file for complete search history.

(56) References Cited

U.S. PATENT DOCUMENTS

| | | | |
|---|---|---|---|
| 4,211,224 A | 7/1980 | Kubach | |
| 4,211,911 A | 7/1980 | Dehn | |
| 4,247,815 A | 1/1981 | Larson | |
| 4,271,389 A | 6/1981 | Jacobi | |
| 4,626,805 A | 12/1986 | Jones | |
| 5,039,824 A | 8/1991 | Takashima | |
| 5,073,782 A * | 12/1991 | Huguenin ............... | G01S 13/89 250/332 |
| 5,101,163 A | 3/1992 | Agar | |
| 5,363,050 A | 11/1994 | Guo | |
| 5,389,735 A | 2/1995 | Bockelman | |
| 5,572,160 A | 11/1996 | Wadell | |
| 5,583,510 A | 12/1996 | Ponnapalli | |
| 5,715,819 A | 2/1998 | Svenson | |
| 5,718,208 A | 2/1998 | Brautigan | |
| 5,774,801 A | 6/1998 | Li et al. | |
| 5,829,522 A | 11/1998 | Ross | |
| 5,859,609 A * | 1/1999 | Sheen ..................... | G01S 13/89 342/179 |
| 6,448,788 B1 | 9/2002 | Meaney | |
| 6,636,816 B1 | 10/2003 | Dvorak et al. | |
| 7,034,548 B2 | 4/2006 | Anderson et al. | |
| 7,148,702 B2 | 12/2006 | Wong et al. | |
| 7,387,010 B2 | 6/2008 | Sunshine | |
| 7,448,880 B2 | 11/2008 | Osaka | |
| 7,668,046 B2 | 2/2010 | Banker | |
| 7,755,010 B2 | 7/2010 | Godshalk | |
| 8,050,740 B2 | 11/2011 | Davis | |
| 8,095,204 B2 | 1/2012 | Smith | |
| 8,494,615 B2 | 7/2013 | Melamed et al. | |
| 8,620,238 B2 | 12/2013 | Chan et al. | |
| 9,176,226 B1 | 11/2015 | Sego | |
| 9,615,765 B2 | 4/2017 | Chayat | |
| 9,948,362 B2 | 4/2018 | Liu | |
| 10,690,760 B2 | 6/2020 | Melamed et al. | |
| 11,092,684 B2 * | 8/2021 | Melamed ................ | G01S 13/89 |
| 2002/0165295 A1 | 11/2002 | Matsumoto | |
| 2003/0146767 A1 | 8/2003 | Steele | |
| 2004/0077943 A1 | 4/2004 | Meaney | |
| 2004/0080448 A1 * | 4/2004 | Lovberg ................ | G01S 13/887 342/179 |
| 2004/0162700 A1 | 8/2004 | Rosenberg et al. | |
| 2004/0174289 A1 * | 9/2004 | Singh ...................... | G01S 13/89 342/179 |
| 2004/0190377 A1 | 9/2004 | Lewandowski | |
| 2005/0040832 A1 | 2/2005 | Steele et al. | |
| 2005/0110672 A1 * | 5/2005 | Cardiasmenos ...... | G01S 13/887 250/330 |
| 2005/0255276 A1 | 11/2005 | Bethune | |
| 2006/0058678 A1 | 3/2006 | Vitek et al. | |
| 2006/0176062 A1 | 8/2006 | Yang et al. | |
| 2006/0220658 A1 | 10/2006 | Okamura | |
| 2008/0296306 A1 | 12/2008 | Handa | |
| 2009/0040099 A1 * | 2/2009 | Young ..................... | G01S 13/89 342/179 |
| 2009/0270718 A1 | 10/2009 | Peter et al. | |
| 2009/0273792 A1 | 11/2009 | Hullin et al. | |
| 2009/0309786 A1 | 12/2009 | Stolpman et al. | |
| 2011/0060215 A1 | 3/2011 | Tupin | |
| 2011/0068807 A1 | 3/2011 | Kesil et al. | |
| 2011/0134001 A1 | 6/2011 | Sakata | |
| 2011/0205583 A1 | 8/2011 | Young et al. | |
| 2011/0227586 A1 | 9/2011 | Lovetri et al. | |
| 2011/0286648 A1 | 11/2011 | Shafir et al. | |
| 2012/0019406 A1 | 1/2012 | Sarkis | |
| 2012/0095343 A1 | 4/2012 | Smith et al. | |
| 2012/0242341 A1 | 9/2012 | Olsson | |
| 2012/0274499 A1 | 11/2012 | Chang | |
| 2012/0327666 A1 | 12/2012 | Liu | |
| 2013/0141287 A1 | 6/2013 | Pallonen | |
| 2013/0231046 A1 | 9/2013 | Pope | |
| 2013/0241780 A1 | 9/2013 | Amm et al. | |
| 2013/0271328 A1 | 10/2013 | Nickel | |
| 2013/0300573 A1 | 11/2013 | Brown | |
| 2013/0329139 A1 | 12/2013 | Feher | |
| 2014/0051976 A1 | 2/2014 | Rapoport et al. | |
| 2014/0066757 A1 | 3/2014 | Naftali | |
| 2014/0176157 A1 | 6/2014 | Melamed | |
| 2014/0179239 A1 | 6/2014 | Nickel | |
| 2014/0212832 A1 | 7/2014 | Fisker et al. | |
| 2014/0218230 A1 | 8/2014 | Ostadrahimi | |
| 2015/0002331 A1 | 1/2015 | Allmendinger et al. | |
| 2016/0336643 A1 | 11/2016 | Pascolini | |

OTHER PUBLICATIONS

Crocco L et al: "Early-stage leaking 1-13 pipes GPR monitoring via microwave A tomographic inversion" Journal of Applied Geophysics. Elsevier. Amsterdam. NL. vol. 67. No. 4. Apr. 1, 2009 (Apr. 1, 2009). pp. 270-277. XP026033856.

Ayliffe et al., 'Electric Impedance Spectroscopy' Using Microchannels with Integrated Metal Electrodes IEEE Journal of Microelectromechanical Systems, vol. 8, No. 1, Mar. 1999.

P. Lombardini et al., "Criteria for the Design of Loop-Type Directional Couplers for the L Band" (1956).

Pallavi R. Malamel et al., "Microwave Reflectometry Based Electrical Characterization of Milk for Adulteration Detection", Advance in Electronic and Electric Engineering, ISSN 2231-1297, vol. 4, No. 5 (2014), pp. 487-492.

Valerie Favry, "Design and Development of a Novel Electronic Sensor for Detecting Mastitis Based On Conductance/Impedance

(56) References Cited

OTHER PUBLICATIONS

Measurements", Thesis submitted for the Degree of Master of Science, Supervised by Prof. Dermot Diamond School of Chemical Sciences, National centre for Sensor Research Jul. 2004.

* cited by examiner

SYSTEM AND METHODS FOR THREE DIMENSIONAL MODELING OF AN OBJECT USING A RADIO FREQUENCY DEVICE

CROSS-REFERENCE

The present application claims the benefit of U.S. Provisional Application Ser. No. 62/157,161, filed on May 5, 2015, entitled "SYSTEM AND METHOD FOR 3D MODELING OF AN OBJECT", the subject matter of the present application is also related to PCT Application PCT/IL2015/050126, filed Feb. 4, 2015, entitled "SYSTEM DEVISE AND METHOD FOR TESTING AN OBJECT", PCT Application PCT/IL2015/050099, filed on Jan. 28, 2015, entitled "SENSORS FOR A PORTABLE DEVICE", U.S. application Ser. No. 14/605,084, filed on Jan. 26, 2015 entitled "VECTOR NETWORK ANALYZER", now U.S. Pat. No. 9,625,508; U.S. application Ser. No. 14/499,505, filed on Sep. 30, 2015 entitled "DEVICE AND METHOD FOR CALIBRATING ANTENNA ARRAY SYSTEMS", now U.S. Pat. No. 9,735,899; U.S. application Ser. No. 14/696,813, filed on Apr. 27, 2015 entitled "PRINTED ANTENNA HAVING NON-UNIFORM LAYERS", now abandoned, each of which is incorporated herein by reference in its entirety. This application is a continuation of U.S. patent application Ser. No. 16/871,397, filed May 11, 2020, now U.S. Pat. No. 11,092,684, which is a continuation of U.S. patent application Ser. No. 15/569,827, filed Oct. 27, 2017, now U.S. Pat. No. 10,690,760, which is a 35 USC 371 National Stage Entry of application PCT/IL2016/050479, filed May 5, 2016, which claims domestic priority to U.S. application 62/157,161, filed May 5, 2015.

INCORPORATION BY REFERENCE

All publications, patents, and patent applications mentioned in this specification are herein incorporated by reference to the same extent as if each individual publication, patent, or patent application was specifically and individually indicated to be incorporated by reference.

FIELD OF THE INVENTION

The present invention relates to a system device and methods for three dimensional (3D) microwave modeling of an object more specifically, but not exclusively, to a Radio Frequency (RF) sensing system for imaging and/or modeling of an object.

BACKGROUND INFORMATION

The 3D imaging and modeling technology is maturing rapidly, affecting the accelerated evolution of a variety of 3D related fields such as 3D printing, gaming, Virtual Reality (VR) and Augmented Reality (AR) etc. 3D printing or Additive Manufacturing (AM) is any of various processes for making a 3D object of almost any shape from a 3D model or other electronic data source primarily through additive processes in which successive layers of material are laid down under computer control. A 3D printer is a type of industrial robot. The 3D printing technology enables the layperson to manufacture small and sophisticated objects without the need for advanced tooling or experts. A 3D printing manufacture may create an original 3D object or copy from another 3D model reference. In both cases there is a need to have accurate mechanical schematics of the object to produce the desired object. A 3D scanner is a device that analyses a real-world object or environment to collect data on its shape and possibly its appearance (e.g. color). The collected data can then be used to construct digital three-dimensional models.

The prior art solutions for modeling objects that are currently used include a system comprising an optical unit, e.g., camera, and providing a 3D image of the object by viewing the object from a number of different angles.

Another solution according to the prior art includes a method for measuring distances to an object using a laser device, and obtaining a 3D contour of the object by turning the object or the laser device. The main disadvantage of this solution is that it only provides an imaging contour of the object and the internal parts are completely obscured. For example the internal parts of an opaque object cannot be imaged and therefore the internal parameters of the object such as size or contour are not provided. Additionally the laser device as provided by the prior art is expensive and may not be sold as a consumer device.

Other prior art solutions include RF systems comprising an RF array for imaging for example for airport security intended to reveal concealed weapons and materials. However, these systems perform planar imaging, i.e., both the array and image reconstruction are plane based, which inhibits full 3D imaging of objects, e.g., limits the imaging of mirror-like objects in angles perpendicular to the array. In addition, these systems do not deal with creating mechanical 3D models of the scanned objects.

The prior 3D modeling such as 3D scanners or devices can be less than ideal in at least some respects. Prior 3D scanners are limited by the ability to scan only the external features of the object. In other words, an output of a 3D modeling of prior art solutions include only the surface of the object, while data relating to the inner sections of the object is missing.

In light of the above, it would be desirable to provide improved methods and apparatus for 3D modeling of an object. Ideally, such methods and apparatus would be easy to use, and provide accurate measurements of the object including the inner parts of the object, for example providing bore dimensions of a flute.

SUMMARY OF INVENTION

Prior to the Summary of the invention being set forth, it may be helpful to set forth definitions of certain terms that will be used hereinafter.

The term '3D modeling' or '3D mechanical model' as used herein is defined as the process of representation of an external and internal parts and parameters (e.g. width, volume etc.) of an object including for example elements which are inside the object.

The term 'RF image' as used herein is defined as an image constructed based on RF signals affected by or reflected from an imaged or scanned object, medium or scene.

The term 'bi static' as used herein is defined as an operation where transmitter and receiver antennas are not co-located (as opposed to mono-static where the transmitter and receiver are co-located).

According to a first aspect of the invention, there is provided a system for generating a three dimension (3D) imaging of an object, the system comprising: an electromagnetic transducer array surrounding the object said array comprising: a plurality of electromagnetic transducers; a transmitter unit for applying RF (radio-frequency) signals to said electromagnetic transducer array; and a receiver unit for receiving a plurality of RF signals affected by said object from said electromagnetic transducers array; a Radio Frequency Signals Measurement Unit (RFSMU) configured to receive and measure said plurality of plurality of affected RF signals and provide RF data of the object; and at least one processing unit, said at least one processing unit is configured to: process said RF data to identify the dielectric properties of said object and construct a 3D image of said object.

In an embodiment, the at least one processing unit is further configured to produce a model of the object, said model comprises a representation of the external and internal shape or parameters of the object.

In an embodiment, the parameters comprise dielectric properties of the object.

In an embodiment, the army is configured to measure the object from a plurality of bi-static angles.

In an embodiment, the plurality of electromagnetic transducers are RF antennas.

In an embodiment, the antennas are selected from a group consisting of flat spiral antennas, printed log periodic antennas, sinuous antennas, patch antennas, multilayer antennas, waveguide antennas, dipole antennas, slot antennas, Vivaldi broadband antennas.

In an embodiment, the wideband electromagnetic transducer array is a MIMO (Multiple Input Multiple Output) antenna array.

In an embodiment, the system comprises a housing having a cavity therein wherein said cavity is configured to contain said object.

In an embodiment, the antenna array is attached to said housing surface.

In an embodiment, the housing shape is selected from the group consisting of: a sphere, a cube, a cage.

In an embodiment, the system comprising motors configured to rotate the housing or the antenna array or the object with respect to Y or X axis.

In an embodiment, the housing comprises at least one arc for holding said plurality of antennas.

In an embodiment, the plurality of antennas are configured to slide up or down along said at least one arc.

In an embodiment, the id plurality of antennas are configured to slide up and down on said arc while the housing is rotated.

In an embodiment, the object is rotated while the housing is in a static position.

In an embodiment, the system comprises a camera, said camera is configured to provide a 2D or a 3D image of the object.

In an embodiment, the 2D or a 3D image of the object are superposed with the 3D image of said object.

According to a second aspect of the present invention there is provided a method for generating a three dimension (3D) image of an object, the method comprising: obtaining a plurality of Radio Frequency (RF) signals from a 3D electromagnetic transducer array surrounding the object, said plurality of RF signals are signals affected by said object or by said object surroundings; measuring the obtained RF signals by a Radio Frequency Signal Measurement Unit (RFSMU) to provide RF data of the object; processing said measured RF data by a processor to remove interferences affecting said RF data; processing the RF data to obtain the dielectric properties of the object; and processing the dielectric properties of the object to construct a 3D visualization of said object.

In an embodiment, the method further comprising calibrating the affected RF signals.

In an embodiment, said array is configured to measure the object from a plurality of bi-static angles.

In an embodiment, the 3D image construction of the object is processed according to delay and sum (DAS) methods.

In an embodiment, the object is a rigid object comprising electromagnetically transparent elements.

In an embodiment, the object is a hollow object.

In an embodiment, the object is made of a material selected from the group consisting of glass, plastic, iron, metal, wood or combination thereof.

In an embodiment, the method comprises obtaining additional information on the object using Synthetic Aperture Radar (SAR) methods.

In an embodiment, the method comprises estimating the location of the array using at least one motion sensor.

In an embodiment, the method comprises dividing the 3D electromagnetic transducer array to a plurality of subarrays and processing separately the RF signals from each subarray by a separate processing unit.

In an embodiment, the method comprises modeling said object, said modeling is obtained by modeling first the external contour of the object and peeling the external modeling and modeling the following internal contour of the object until the inner parts of the object are completely modeled.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples arc illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks, according to embodiments of the invention, could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein, are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

The subject matter disclosed may best be understood by reference to the following detailed description when read with the accompanying drawings in which.

DETAILED DESCRIPTION OF THE INVENTION

Figure 1:
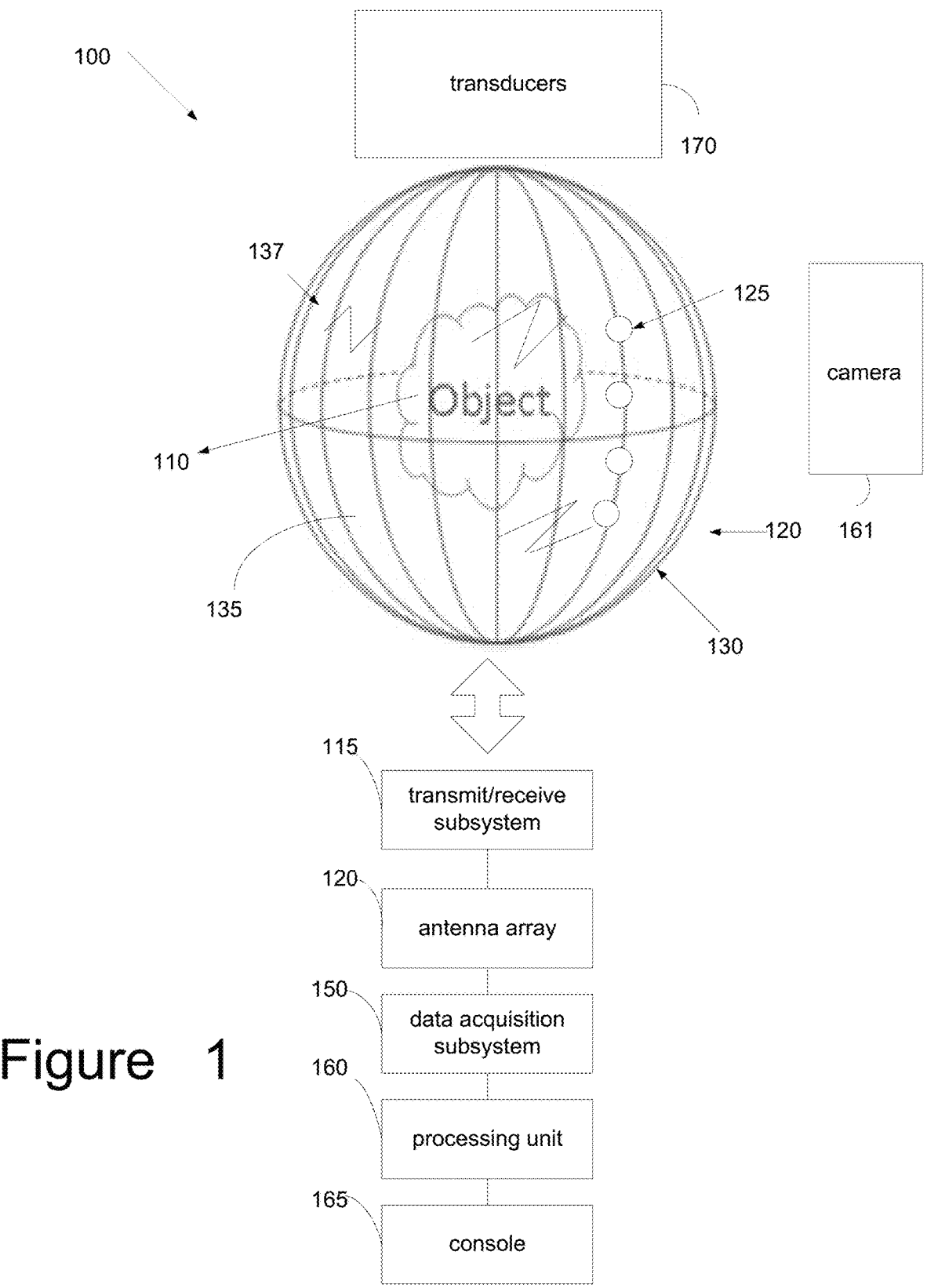
FIG. 1 is a diagram of a 3D scanning and/or imaging system, according to an embodiment of the invention.

The present invention, in some embodiments thereof, relates to RF radiation methods, devise and system such as microwave or millimeter-wave methods for imaging and/or modeling an object. More specifically, but not exclusively, the present invention relates to a system, device and methods for providing a 3D mechanical model, of objects such as 3D objects.

Additionally, embodiments of the present invention provide 3D data, such as 3D image data or modeling on the internal structure of an object such as data of the inner sections or elements of the object for example data relating to nonmetallic objects materials, such as plastics, glass, wood, etc. In other words, while 3D modeling image data according to the prior art includes only the contour of the object, eliminating data relating to latescent parts of the object, the present invention methods and devices are configured to provide data on hidden parts of the object, such as internal structure of opaque objects.

In some cases, device and methods according to the invention are configured to reproduce or model the surface and inner parts of an object wherein some of the object's parts are concealed and therefore may not be measured according to prior art devices or methods without damaging the copied object.

According to some embodiments of the present invention, there is provided a system for constructing a 3D representation or image (e.g. visualization) of an object for example a virtual 3D representation (e.g. 3D image) of an object.

The system comprises a plurality of transducers (e.g. electromagnetic transducers); a transmitter unit for applying RF (radio-frequency) signals to said electromagnetic transducer array; and a receiver unit for receiving a plurality of RF signals affected by said object from said electromagnetic transducers array; a Radio Frequency Signals Measurement Unit (RFSMU) configured to receive and measure said plurality of plurality of affected RF signals and provide RF data of the object based on the plurality of affected RF signals; and at least one processing unit configured to: process said RF data to identify the dielectric properties of said object and construct a 3D visualization (e.g. image) of said object.

Specifically, the system comprises a sensing unit, the sensing unit comprises an antenna array comprising a plurality of antennas, the antennas are configured to radiate high frequency RF signals. The system further includes a transmitter module (sub-system), a receiver module (sub-system) and at least one processing unit for processing the measured signals and constructing the 3D image of the object. The 3D image may comprise 3D representation of the surface and internal sections of the object.

By augmenting the bistatic imaging with near field 3D imaging and modeling of the external and internal structure of multi layered complex bodies the present invention embodiments may provide even more accurate models which can be used for various applications, including, but not limited to, 3D printing and non-destructive testing (NDT).

According to another embodiment of the invention the imaging system may include a number of electromagnetic mirrors for diversifying the viewing angles and imaging the object from multiple viewing angles. For example, scanning an object from a front hemisphere while having a mirror behind the object allows imaging the back side of the object as well.

Reference is now made to FIG. 1 which is a schematic diagram illustrating a system 100 for constructing a 3D representation of an object 110 according to one embodiment of the invention. The system 100 comprises one or more sensors, specifically the system comprises an array of transducers for example one or more 3D multi-antenna arrays configurations 120 which surrounds an object 110 (hereinafter OUT or MUT or sample or material(s) or substance(s)). For example, the object may be hermetically surrounded by the array. The antenna array 120 comprises a plurality of antennas 125. The antennas can be of many types known in the art, such as flat spiral antennas, printed log periodic antennas, sinuous antennas, patch antennas, multilayer antennas, waveguide antennas, dipole antennas, slot antennas, Vivaldi broadband antennas. The antenna array can be a MIMO or a linear or two-dimensional, flat or conformal to the region of interest.

In some cases, the system 100 comprises a housing for holding the antenna array. For example, the housing may be a cage 130, shaped as a spherical cage or other shape such as a cube for holding the antenna array and surrounding the object. The cage 130 comprises one or more arcs 135 for holding the antennas 125. For example, the object may be hermetically surrounded by the housing.

In some cases, the housing may include an opening for inserting the object to the cage and a holding for holding the object.

The antenna array 120 may transfer a plurality of RF signals 137 propagating a wave into the cage 130 for constructing a 3D image of the object. The system 100 further includes a transmit/receive subsystem 115 configured to generate and transmit the RF signals, for example, from 10 MHz to 10 GHz, a Radio Frequency Signals Measurement Unit (RFSMU) 120 such as a Vector Network Analyzer (VNA) for measuring the received/reflected signals, a data acquisition subsystem 150 and further at least one processing unit 160 for processing the measured signals to provide an RF image and further a 3D visualization (e.g. one or more 3D images) of said object.

The transmit/receive subsystem 115 is responsible for generation of the RF signals, coupling them to the antennas, reception of the RF signals from the antennas and converting them into a form suitable for acquisition. The signals can be pulse signals, stepped-frequency signals, chirp signals and the like. The generation circuitry can involve oscillators, synthesizers, mixers, or it can be based on pulse oriented circuits such as logic gates or step-recovery diodes. The conversion process can include down conversion, sampling, and the like. The conversion process typically includes averaging in the form of low-pass filtering, to improve the signal-to-noise ratios and to allow for lower sampling rates.

According to some embodiments of the invention, the transmit/receive subsystem 115 may perform transmission and reception with multiple antennas at a time or select one transmit and one receive antenna at a time, according to a tradeoff between complexity and acquisition time.

The data acquisition subsystem 150 collects and digitizes the signals from the transmit/receive subsystem 115 while tagging the signals according to the antenna combination used and the time at which the signals were collected. The data acquisition subsystem 150 will typically include analog-to-digital (A/D) converters and data buffers, but it may include additional functions such as signal averaging, correlation of waveforms with templates or converting signals between frequency and time domain.

In an embodiment, the data acquisition subsystem 150 may include signal source/s, amplifiers, mixers, antennas, analog to digital converters, data transfer HW, memory, controller, power delivery hardware, and all other components required.

The processing unit 160 is responsible for converting the collected RF signals into responses and merging other data such as image data received from optical sensors such as the camera or the ultrasound units, and converting the sets of RF responses and image data, into data to reconstruct a 3D image as will be described in details herein below. The processing unit 160 is usually implemented as a high-performance computing platform, based either on dedicated Digital Signal Processing (DSP) units, general purpose CPUs, or, according to newer trends, Graphical Processing Units (GPU).

A final step in the process is making use of the resulting image, either in the form of visualization, display, storage, archiving, or input to feature detection algorithms. This step is exemplified in FIG. 1 as console 165. The console may be part of a mobile device and is typically implemented as a handheld computer such as a mobile telephone or a table computer with appropriate application software.

In some cases, the system 100 may include an optical device such as an optical camera 161 configured to image and model the contour of the object 110 (e.g. provide an optical image), and characterize the visual characteristics of the object, e.g., its colors. The contour obtained from the optical device (e.g. the camera 161) may be fused or superposed with the contour of the RF image as provided by the antenna array to get a more precise model of the object.

The camera may be a CCD or CMOS camera.

For example, the constructed 3D image processed by the processing unit based on measurements and analysis of the RF signals reflected from the object may be merged with an external 3D contour obtained from the 2D or 3D images.

In some cases, the superposition process may be utilized as part of a calibration process of the array. The visual information about the exterior of the 3D object may be used to refine the accuracy of the microwave imaging system.

Examples for embodiments for a calibration process may be found in U.S. patent application Ser. No. 14/499,505, filed on Sep. 30, 2015 entitled "DEVICE AND METHOD FOR CALIBRATING ANTENNA ARRAY SYSTEMS" which application is incorporated by reference herein in its entirety.

In some cases, system 100 may include ultrasound transducers 170, and the processing unit may fuse the resulting reconstructed ultrasound image with the RF image and or the optical image.

The merging process of the different type of images (e.g. the RF image and other type of images such as ultrasound image) may include an optimization step to improve and/or to optimize 3D image reconstruction time. The optimization may include variable resolution imaging, e.g., reconstructing a crude image, which is then further processed to enhance resolution only in these relevant regions.

The basic principle of operation of the system 100 is as follows. RF signals are radiated by the transmit/receive subsystem 115, via the antenna army 120, and are further reflected by the object 110 or transmitted through it, and received by the transmit/receive subsystem 115. At the next step the received signals are generated and received at RFSMU 120. The received signals are then processed at the processing unit 160 resulting in a reconstructed 3D image.

Once a reconstructed image is available, further processing is carried out in order to distill a 3D mechanical model of the contour as well as the internal structure of the multi-layered object as will be described in detail hereinbelow.

Figure 2:
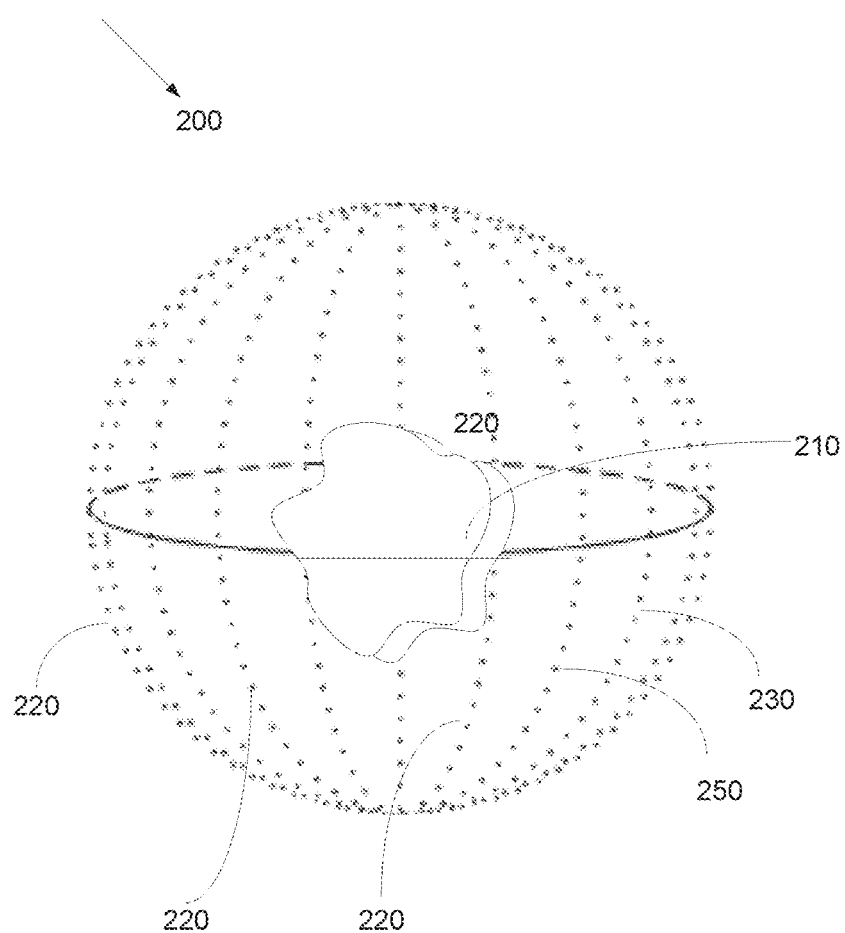
FIG. 2 is a diagram of a sphere shaped transducer 3D array according to some embodiments of invention.

Reference is now made to FIG. 2 illustrating a sphere-shaped transducer (e.g. antenna) army 200 covering a surface of a housing 230, shaped as a ball, and surrounding an object 210 according to one embodiment of the invention. The housing shape may include, but is not limited to, a ball, cube, a cage and so on. The housing may be in the form of a spherical cage comprising a plurality of arcs 220. The transducer (e.g. antenna) array 200 comprises a plurality of transducers (e.g. antennas) 250 (e.g. transmit and receive antennas) covering the housing's surface. In some cases, the plurality of antennas are attached along the housing's arcs. The antenna army 200 is configured to cover all bi-static angles of transmit and receive from multiple possible viewing angles of the object. It is stressed that covering multiple bi-static angles is crucial since many objects behave as "mirrors" for the relevant wavelengths, and therefore the energy is reflected to a localized angle in space. The antenna array topology as shown in FIG. 2 is configured to collect all Tx and Rx angles instantaneously.

According to embodiments of the invention the antenna array is configured to receive signals reflected from the object as well as signals transmitted through the object. For example the signals may be received by an Rx antenna, and transferred through an analog path (e.g. amplifier, mixer, filter), sampled by the analog to digital converter, digitally processed (e.g. filters, weighting) of the processing unit and transferred to the next level.

Figure 3:
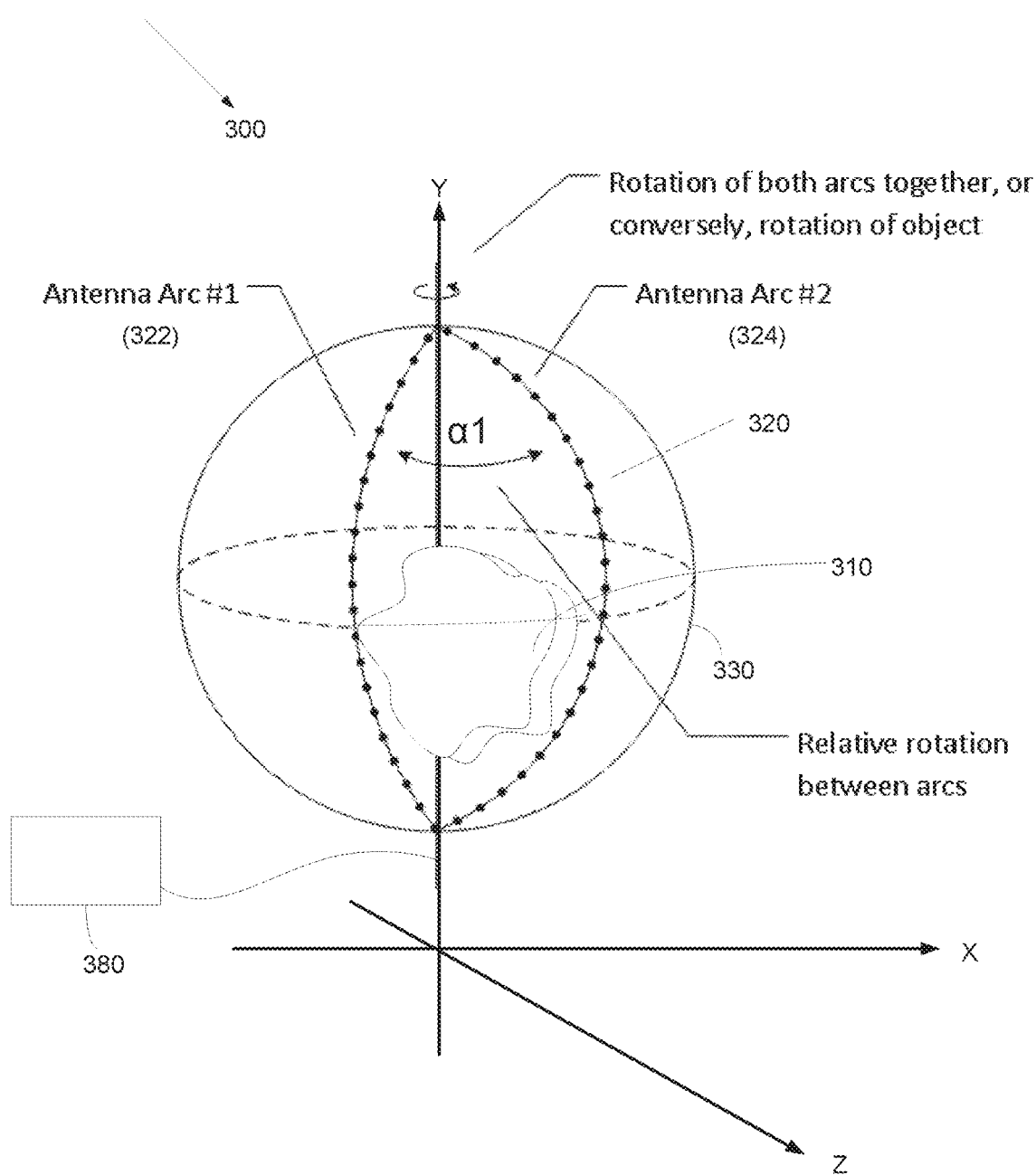
FIG. 3 is a diagram of a sphere 3D army comprising two arcs, according to an embodiment of the invention.

Reference is now made to FIG. 3 illustrating a system such as an imaging system 300 according to another embodiment of the invention. The system 300 comprises an antenna array 320 comprising a plurality of antennas (e.g. transmit and receive antennas) which may be mounted on a housing 330, shaped for example as spherical ball or cage. The housing may include one or more arcs for holding the plurality of antennas and a driver and rotation unit 380 for rotating the housing and/or the arcs and/or the object along a rotation axis Y parallel to the arcs in respect to an X-, Y-, Z-axis Cartesian coordinate system. Specifically, the housing 330 may include two antenna arcs (e.g. antenna arc 322 and antenna arc 324) comprising a plurality of antenna. For example, the two arcs, may comprise any angle of rotation in respect to axis Y while the object is static.

In some cases, the arcs 322 and 324 may be at a distance al with respect to axis X along the housing 330 diameter. Advantageously, the rotation configuration as illustrated in FIG. 3 enables to reduce the required number of antennas in the antenna array by rotating the antenna array (e.g. arcs 322 and 324) or the object.

The rotation unit 380 may be controlled by controller which may determine the rotation speed of the antenna and also the object. For example, the housing may be rotated in a speed of several degrees or tens of degrees per second.

In accordance with embodiments as illustrated in FIG. 3, system 300 is configured to measure the object 310 from all bi-static angles while utilizing a small number of antennas (e.g. receiving and transmitting antennas), for example fewer transmitters and receivers antenna than the number of antennas included in system 200 shown in FIG. 2 (for example less than 10 antennas or only two antennas). However, the measurements provided by the system 300 are not instantaneous and the antennas of FIG. 3 must be swept (e.g. rotated) over all positions and angles. By rotating the arcs (e.g. arc 324 or 322) the system may cover multiple bi-static angles which result in all possible angles between the transmitter and receiver, and all transmitter to object angles.

In one embodiment, the system 300 may include two rotation states for imaging or modelling the object 310, in accordance with embodiments of the invention.

In a first rotation state object 310 is rotated while the housing 330 and the antennas are in a fixed position, imaging the object. Alternatively, the object may be in a fixed position while the housing 330 may be rotated for example anticlockwise in respect to axis Y and imaging the object from all possible angels. Optionally, both the object and housing may be rotated synchronically for imaging the object from all possible angles.

In a second rotation state the angle α1 between the arcs (e.g. arcs 322 and 324) may be controlled, for example the first arc, such as arc 322 may be static, while the second arc (e.g. 324) may be rotated to or from the first arc in respect to the Y axis.

In some cases, the housing may be rotated in respect to the Y axis and or the X axis.

According to some embodiments of the invention the system 300 may include more than two arcs, for example the system 300 may include a plurality of arcs, for example at a distance α1 between two consecutive arcs where α1 may be 1, 2, 3, 4, 5, 6, 7, 8, 9, 10 or more degrees. In some cases, the system may include partial arcs, for example the system may include a single arc covering 180 degrees (e.g. half of spherical ball) or two arcs where each arc is configured to cover complementary 90 degrees, (both arcs covering the 180 degrees).

Figure 4:
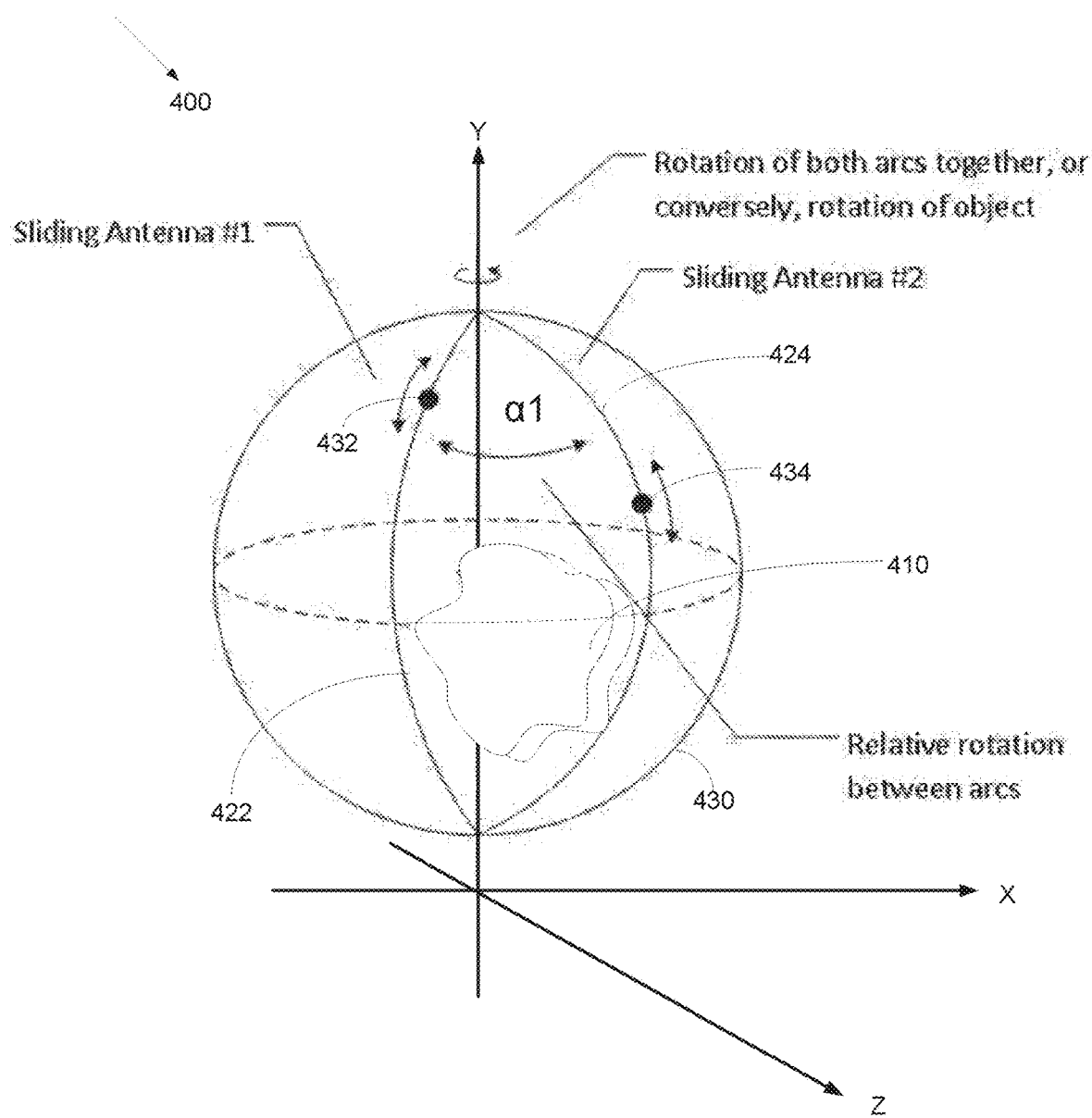
FIG. 4 is a diagram of a sphere antenna array including two antennas, according to some embodiments of the invention.

Reference is now made to FIG. 4 illustrating a system 400 for imaging and further modelling an object 410, in accordance with embodiments of the invention. The system 400 may comprise a limited number of antennas, for example only two antennas configured to cover all bi-static angles of the object.

The system 400 comprises a housing 430, shaped as spherical cage, and surrounding the object 410. According to embodiments of the invention the antenna may be attached to the hosing. For example, may be in the form of a spherical cage comprising a plurality of arcs 220, where each arc is configured to hold at least one antenna.

In some cases, as shown in FIG. 4, the imaging system 400 comprises a first antenna 432 and a second antenna 434, where each antenna may be located at any point on the surface of the sphere. For example, the first antenna 432 may be attached to a first arc 422 while the second antenna 434 may be attached to a second arc 424. In an embodiment both antennas, the first antenna and the second antenna, may slide up and down accordingly and synchronically while the sphere is rotated.

Figure 5A:
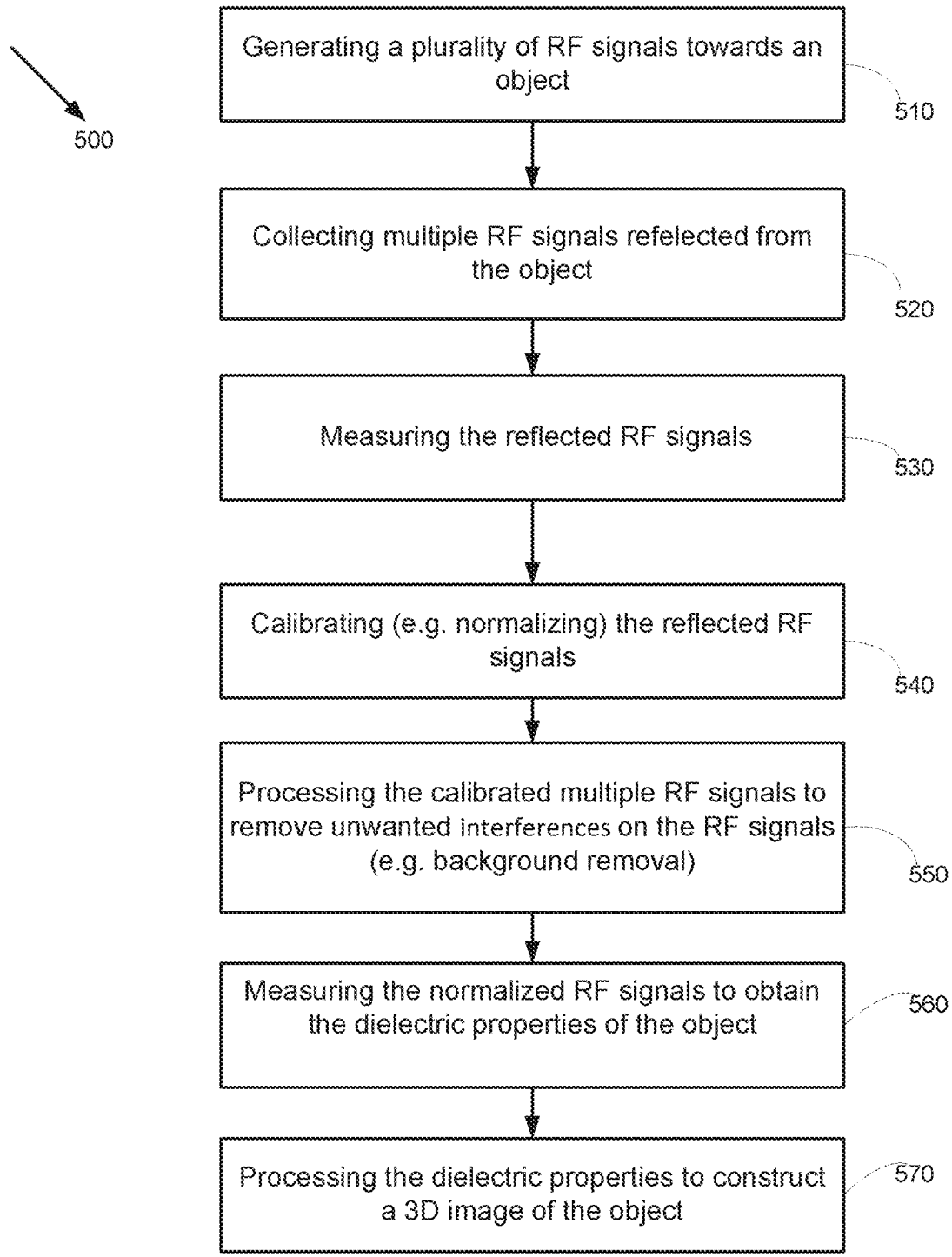
FIGS. 5A-5B are flowcharts of methods for 3D scanning and modeling of an object, according to some embodiments of the present invention.

Reference is now made to FIG. 5A illustrating a flowchart 500 of a method of 3D image reconstruction and modelling of an object using a RF device, in accordance with embodiments of the invention.

At step 510 one or more RF signals, for example between 2 GHz and 9 GHz, are generated by one or more RF transducers (e.g. sensors or antenna), such as the antenna array attached to or placed on the housing comprising the object as illustrated in FIGS. 1-4. The signals are emitted towards the object, preferably from all (or almost all) bi-static angles. The RF sensors may be any of the mentioned above sensors.

At step 520 the multiple RF signals reflected or affected from or by the object and/or the scene surrounding the scene are obtained from all (or almost all) bi-static angles by the RF sensors and at step 530 the reflected or affected RF signals are measured, for example by the RFSMU 120 to obtain RF data of the object.

In an embodiment, the emitted and affected signal of steps 510 and 520 are transmitted and obtained from a plurality of angles by rotating the object and/or the RF transducers as illustrated in FIGS. 1-4.

At step 540 a calibration process is carried out to tune the imaging system so as to maintain coherency of the signals throughout the frequency range, over the entire array, and over all the measurements (e.g. in the case of non-instantaneous measurements).

The methods, system and apparatus disclosed herein are capable of calibrating an antenna or an antenna array, such as the array or antennas illustrated in FIGS. 1-4, by utilizing one or more targets. The calibration process is required for example, for each pair of bi-static antennas and for each frequency. The methods and apparatus can be configured to measure the electronic delay and possible mismatch between the antennas and/or the electronics of the array or the device comprising the array, and possible mismatch between the antenna and the medium (object under test).

The targets' properties used for calibrating the antenna array may be known, unknown or partially known. For example, the target may be any object which it's electromagnetic (EM) response may be measured, such as a metal ball.

Methods and system according to embodiments of the invention include measuring the EM reflections of the target, located in a specific location in respect to the antenna array and analyzing the reflected EM signal to configure a separated EM transmit response (e.g. forward term) and receive response (e.g. reverse term) for each antenna of the antenna array. A further analysis process includes comparing (e.g. simulating) the calculated EM responses to a set of responses which should have been received and configuring the array's full complex EM response (e.g. the antennas EM responses reflected from the medium in time and frequency).

In addition, accurate chip-level calibrations are required in order to guarantee the stability and linearity of the recorded signals.

Examples for calibrating an antenna may be found in PCT Patent Application No. PCT/FL2016/050444 entitled SYSTEM AND METHODS FOR CALIBRATING AN ANTENNA ARRAY USING TARGETS which application is incorporated by reference herein in its entirety.

At step 550, a background removal process is applied on to remove unwanted interferences received at the antenna.

At step 560, the normalized RF signals are measured to obtain the dielectric properties of the object and identify the quantitative qualities of the object. The processing step may be activated for example by the processor unit and the Radio Frequency Signals Measurement Unit (RFSMU) connected to or in communication with the sensors as shown in FIG. 1.

Examples of methods for measuring the dielectric properties of an object and identifying the quantitative qualities of the object may be found in the present applicant patent applications and patents, for example PCT Application number PCT/IL2015/050126, filed Feb. 4, 2015, entitled "SYSTEM DEVISE AND METHOD FOR TESTING AN OBJECT", PCT Application PCT/IL2015/050099, filed on Jan. 28, 2015, entitled "SENSORS FOR A PORTABLE DEVICE" and U.S. Pat. No. 8,494,615 filed Mar. 18, 2011 which applications and patent is incorporated by reference herein in its entirety.

At step 570 a 3D image reconstruction process of the object is initiated by the processing unit 160. In an embodiment, the reconstruction process includes analysis of the RF data (e.g. dielectric properties of the object) by the processing unit using processing methods such as delay and sum (DAS) methods. Specifically, according to embodiments of the invention, a 3D image of the object is reconstructed based on arbitrary antenna arrays, such as antenna army 120 of FIG. 1 or the antennas of FIGS. 2-4, according to a DAS beamforming method. As follows: After having transmitted from all, or some, of the sensors and having received with all or some of the remaining sensors, the reflected or affected RF signals are converted to time domain. Let $y_{ij}(t)$ denote the time domain signal obtained when transmitting from sensor i and receiving in sensor j. According to the DAS method, to obtain the image at point r in space, the signals are delayed according to the expected delay from the pair of sensors to point r, denoted $T_{ij}(r)$ and then summed, yielding Eq (1):

$$I_{DAS}(r)=\Sigma_{ij}y_{ij}(T_{ij}(r)) \quad (1)$$

The DAS algorithm requires adaptations to handle sensor radiation pattern and frequency responses of the various system components (RF elements, traces, sensors).

In addition, the signal acquisition may be performed in time domain, or rather, it may be performed in frequency domain, over discontinuous frequency windows. Furthermore, possibly, every frequency region uses a different set of sensors and has a different gain and noise properties. The selection of these frequency windows comes hand in hand with the array design, where the angular diversity of the array compensates for the missing information in frequency, and vice versa.

In general, coherent combining of the signals may be performed in frequency domain, with predefined weights according to Eq 2:

$$I_{coh}(r)=\Sigma_{ij}\Sigma_f Re\{w_{ij}(f;r)\cdot Y_{ij}(f)\} \quad (2)$$

Where $w_{ij}(f;r)$ is the complex weight given to frequency f in pair i→j when imaging point r. The value of $w_{i,j}$ is computed while taking into account the following considerations:

The contribution of various sensor pairs/sub-arrays and different frequencies to the resolution. For example, if there are fewer low-frequency sensors, their signals will be amplified in order to balance their power and improve resolution.

Compensation of the gain and frequency response of different frequency regions/windows.

Path loss and lossy materials: weak signals that result from space/material loss are amplified, in general, as long as they are above the noise/clutter level.

Known properties of the antennas/sensors (e.g. radiation pattern and frequency response) and of the path and the target (e.g. spatial and spectral response of a Rayleigh reflector).

Adaptive imaging (such as capon beamforming) may be applied. In this case the weights $w_{ij}$ are determined based on the measured signals, e.g. in order to optimize SNR or signal to clutter in a given location on the image Transparent Objects In some cases, the object such as object 110 or 210 of FIGS. 1-2, may include a specific structure, which requires a more challenging solution to construct a 3D image of these objects. Specifically, imaging objects comprising rigid man-made and half-transparent bodies, for example hollow objects made of glass or plastic. This is a result of these objects smooth surfaces which operate like mirrors at small wavelengths (i.e., where the wavelength is substantially smaller that the roughness of the surface). Unlike point scatters, most of the energy in these objects is reflected along a specific direction. In this case the resolution cannot be obtained by simply summing all sensor pairs (such as $I_{DAS}(r)$), and different bi-static measurements of the surface have to be utilized. Furthermore, the object's rigid body distorts the signals obtained from deeper layers (e.g. cavities). Due to the high sensitivity of the system (e.g. such as system 100) to the propagation velocity and the width of the materials between the imaged body and the antenna, the surface and in some cases the material properties have to be estimated prior to imaging of the internal layers.

Image Improvements

According to further embodiments of the invention, the number of different signals and viewing angles, and hence image quality and resolution of the object, can be improved by using additional imaging methods and devices such as Synthetic Aperture Radar (SAR) methods. According to SAR methods the array elements or the object may be moved, as illustrated in FIGS. 1-4 The information can be combined either at the signal level (i.e. extending $I_{coh}$ by adding synthetic pairs), or at the image level (i.e. by coherently combining images obtained from different angles). The location of the array can be estimated using one or more motion sensors and the signals themselves (e.g. with respect to a reference target or a reference antenna).

However, the imaging complexity, using additional imaging methods such as SAR, is increased since the image resolution and the required number of sensors is increased in proportion to one over the wavelength. To cope with the increased imaging complexity several techniques may be applied. According to a first embodiment, the antenna array may be divided to subarrays, where the information from each subarray is processed separately by a separate processing unit or by a single processing unit such as unit 160 and then combined by the processing unit once the image is constructed at the image reconstruction step.

Alternatively or on combination, a variable resolution imaging process may be used. The variable resolution imaging process comprises producing a low resolution image, for example a resolution of between and then identifying the "interesting" parts of the image and improving resolution only in those parts. In some cases, the 'interesting parts' are defined as such as and are located according to methods such.

Furthermore, according to some embodiments of the invention as part of the step for reconstruction the image, the regularities in the antenna arrays may be utilized in order to reduce the number of computations (using FFT-like structures).

In some cases, polarimetric information, obtained from cross- and co-polarized sensors may be utilized in order to estimate properties, of the object which are not visible by unipolar imaging, for example, structures and details which lie below the imaging resolution.

In another embodiment, known imaging methods such as Capon or various adaptive beamforming methods may be utilized in order to improve image quality and/or signal to clutter ratio. The reconstructed image may be improved by an iterative process, which extracts important physical parameters, e.g., dielectric properties, and reuses them to improve the image.

Figure 5B:
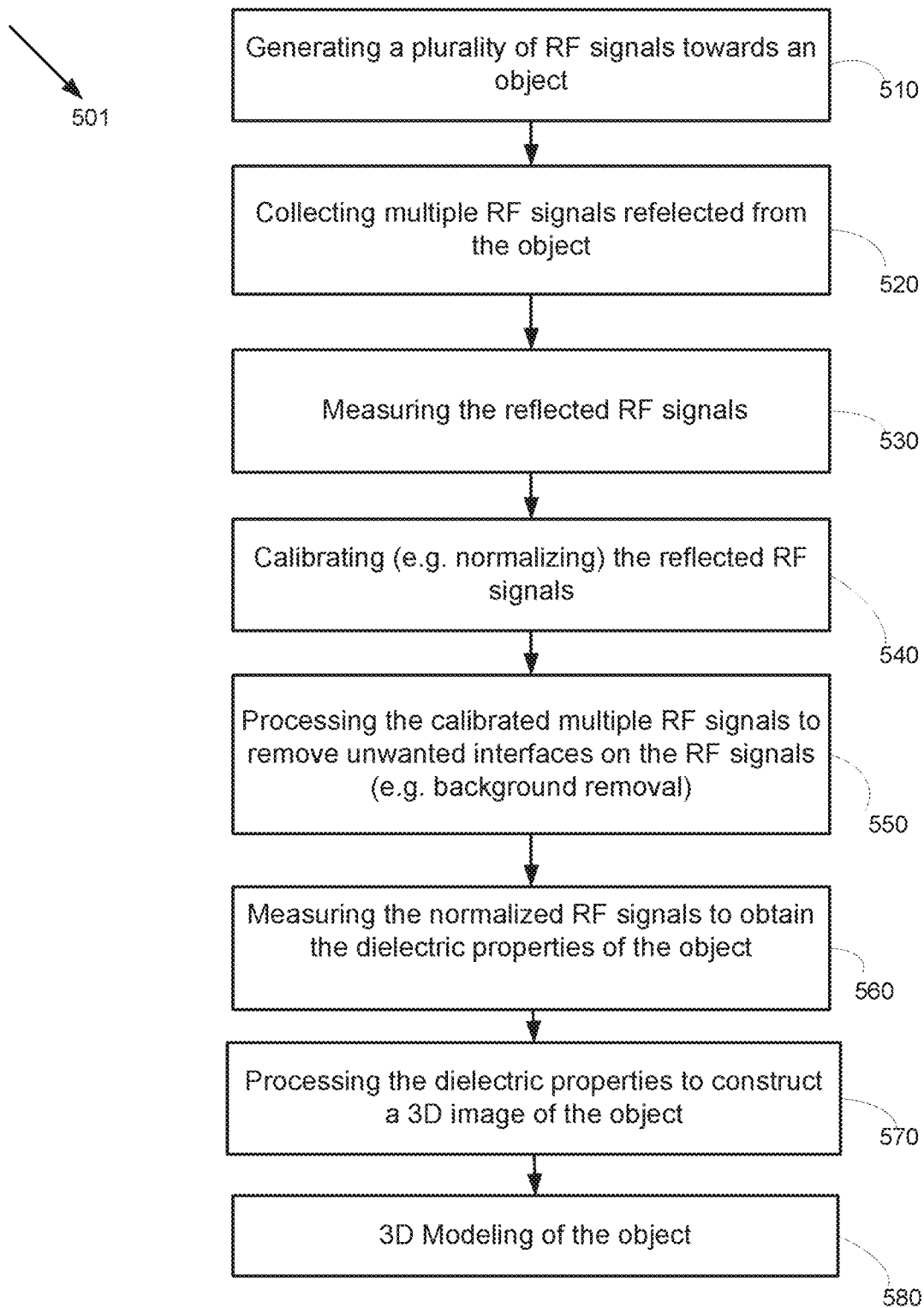

FIG. 5B is a flowchart of a method 501 of a method for 3D modelling of an object, in accordance with embodiments of the invention. Method 501 comprises all steps for constructing a 3D image as illustrated in flowchart 500 of FIG. 5A. Once the reconstructed image is obtained at step 570, a 3D modelling of the object is obtained at step 580, resulting in a mechanical 3D model of the object. According to one embodiment of the invention the external contour of the object is first modeled which follows by a "peel" of the external model and modeling the followed internal contour of the object such as in an onion peeling process, step by step until the inner parts of the object are completely modeled. The reconstruction stage includes a combination of transmission imaging, i.e., using the signals which passed through the object, and reflection imaging, i.e., the signals which are reflected back from the object. According to some embodiments, polarimetric data may be exploited as well.

According to some embodiments, the object may be inserted into a high epsilon material, in order to improve resolution, resulting in an effective shorter wavelength than in air.

Figure 6:
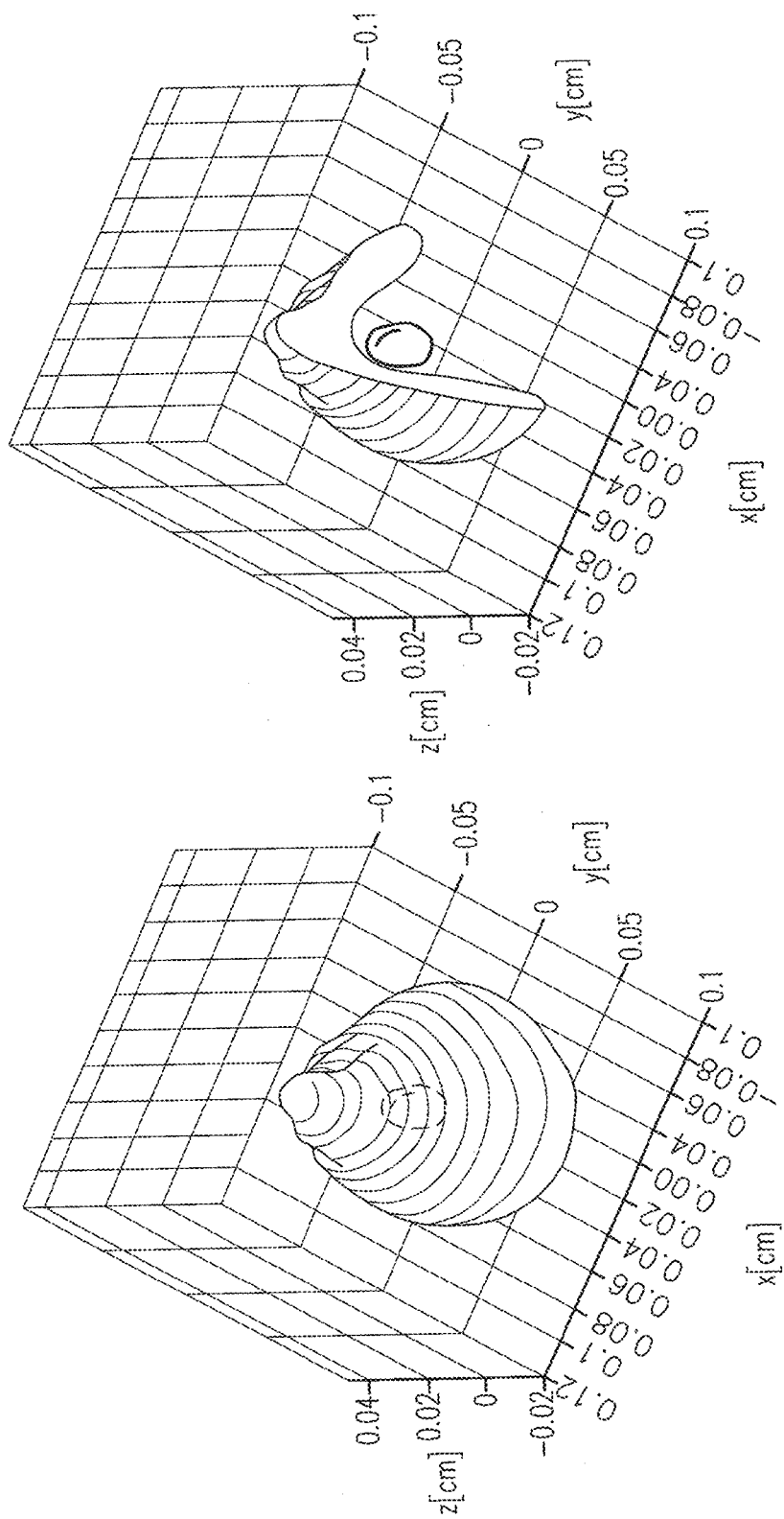
FIG. 6 is a 3D cross section image of a solid opaque cup and a ball inside the cup, according to some embodiments of the present invention.

Reference is now made to FIG. 6 illustrating a 3D cross section image of a solid opaque cup and a ball inside the cup where both the ball and the cup are visible. The present invention provides a system and method for modeling an object which includes providing a representation of the external and internal parts and parameters (e.g. width, volume etc.) of the object including for example elements which are inside the object such as the ball shown in FIG. 6.

The terms "comprises", "comprising", "includes", "including", "having" and their conjugates mean "including but not limited to". This term encompasses the terms "consisting of" and "consisting essentially of".

As used herein, the singular form "a", "an" and "the" include plural references unless the context clearly dictates otherwise.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

In further embodiments, the processing unit may be a digital processing device including one or more hardware central processing units (CPU) that carry out the device's functions. In still further embodiments, the digital processing device further comprises an operating system configured to perform executable instructions. In some embodiments, the digital processing device is optionally connected a computer network. In further embodiments, the digital processing device is optionally connected to the Internet such that it accesses the World Wide Web. In still further embodiments, the digital processing device is optionally connected to a cloud computing infrastructure. In other embodiments, the digital processing device is optionally connected to an intranet. In other embodiments, the digital processing device is optionally connected to a data storage device.

In accordance with the description herein, suitable digital processing devices include, by way of non-limiting examples, server computers, desktop computers, laptop computers, notebook computers, sub-notebook computers, netbook computers, netpad computers, set-top computers, handheld computers, Internet appliances, mobile smartphones, tablet computers, personal digital assistants, video game consoles, and vehicles. Those of skill in the art will recognize that many smartphones are suitable for use in the system described herein. Those of skill in the art will also recognize that select televisions with optional computer network connectivity are suitable for use in the system described herein. Suitable tablet computers include those with booklet, slate, and convertible configurations, known to those of skill in the art.

In some embodiments, the digital processing device includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. Those of skill in the art will also recognize that suitable mobile smart phone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®.

In some embodiments, the device includes a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). In other embodiments, the device is a storage device including, by way of non-limiting examples, CD-ROMs, DVDs, flash memory devices, magnetic disk drives, magnetic tapes drives, optical disk drives, and cloud computing based storage. In further embodiments, the storage and/or memory device is a combination of devices such as those disclosed herein.

In some embodiments, the digital processing device includes a display to send visual information to a user. In some embodiments, the display is a cathode ray tube (CRT). In some embodiments, the display is a liquid crystal display (LCD). In further embodiments, the display is a thin film transistor liquid crystal display (TFT-LCD). In some embodiments, the display is an organic light emitting diode (OLED) display. In various further embodiments, on OLED display is a passive-matrix OLED (PMOLED) or active-matrix OLED (AMOLED) display. In some embodiments, the display is a plasma display. In other embodiments, the display is a video projector. In still further embodiments, the display is a combination of devices such as those disclosed herein.

In some embodiments, the digital processing device includes an input device to receive information from a user. In some embodiments, the input device is a keyboard. In some embodiments, the input device is a pointing device including, by way of non-limiting examples, a mouse, trackball, track pad, joystick, game controller, or stylus. In some embodiments, the input device is a touch screen or a multi-touch screen. In other embodiments, the input device is a microphone to capture voice or other sound input. In other embodiments, the input device is a video camera to capture motion or visual input. In still further embodiments, the input device is a combination of devices such as those disclosed herein.

In some embodiments, the system disclosed herein includes one or more non-transitory computer readable storage media encoded with a program including instructions executable by the operating system of an optionally networked digital processing device. In further embodiments, a computer readable storage medium is a tangible component of a digital processing device. In still further embodiments, a computer readable storage medium is optionally removable from a digital processing device.

In some embodiments, a computer readable storage medium includes, by way of non-limiting examples, CD-ROMs. DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media. In some embodiments, the system disclosed herein includes at least one computer program, or use of the same. A computer program includes a sequence of instructions, executable in the digital processing device's CPU, written to perform a specified task. Computer readable instructions may be implemented as program modules, such as functions, objects, Application Programming Interfaces (APIs), data structures, and the like, that perform particular tasks or implement particular abstract data types. In light of the disclosure provided herein, those of skill in the art will recognize that a computer program may be written in various versions of various languages.

The functionality of the computer readable instructions may be combined or distributed as desired in various environments. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof.

In some embodiments, a computer program includes a mobile application provided to a mobile digital processing device. In some embodiments, the mobile application is provided to a mobile digital processing device at the time it is manufactured. In other embodiments, the mobile application is provided to a mobile digital processing device via the computer network described herein.

In view of the disclosure provided herein, a mobile application is created by techniques known to those of skill in the art using hardware, languages, and development environments known to the art. Those of skill in the art will recognize that mobile applications are written in several languages. Suitable programming languages include, by way of non-limiting examples, C, C++, C#, Objective-C, Java™, Javascript, Pascal, Object Pascal, Python™, Ruby, VB.NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator®, Celsius, Bedrock, Flash Lite, NET Compact Framework, Rhomobile, and WorkLight Mobile Platform. Other development environments are available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Those of skill in the art will recognize that several commercial forums are available for distribution of mobile applications including, by way of non-limiting examples, Apple® App Store, Android™ Market, BlackBerry® App World, App Store for Palm devices, App Catalog for webOS, Windows® Marketplace for Mobile, Ovi Store for Nokia® devices, Samsung® Apps, and Nintendo® DSi Shop.

In some embodiments, the system disclosed herein includes software, server, and/or database modules, or use of the same. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

In some embodiments, the system disclosed herein includes one or more databases, or use of the same. In view of the disclosure provided herein, those of skill in the art will recognize that many databases are suitable for storage and retrieval of information as described herein. In various embodiments, suitable databases include, by way of non-limiting examples, relational databases, non-relational databases, object oriented databases, object databases, entity-relationship model databases, associative databases, and XML databases. In some embodiments, a database is internet-based. In further embodiments, a database is web-based. In still further embodiments, a database is cloud computing-based. In other embodiments, a database is based on one or more local computer storage devices.

In the above description, an embodiment is an example or implementation of the inventions. The various appearances of "one embodiment," "an embodiment" or "some embodiments" do not necessarily all refer to the same embodiments.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Reference in the specification to "some embodiments", "an embodiment", "one embodiment" or "other embodiments" means that a particular feature, structure, or characteristic described in connection with the embodiments is included in at least some embodiments, but not necessarily all embodiments, of the inventions.

It is to be understood that the phraseology and terminology employed herein is not to be construed as limiting and are for descriptive purpose only.

The principles and uses of the teachings of the present invention may be better understood with reference to the accompanying description, figures and examples.

It is to be understood that the details set forth herein do not construe a limitation to an application of the invention.

Furthermore, it is to be understood that the invention can be carried out or practiced in various ways and that the invention can be implemented in embodiments other than the ones outlined in the description above.

It is to be understood that the terms "including", "comprising", "consisting" and grammatical variants thereof do not preclude the addition of one or more components, features, steps, or integers or groups thereof and that the terms are to be construed as specifying components, features, steps or integers.

If the specification or claims refer to "an additional" element, that does not preclude there being more than one of the additional element.

It is to be understood that where the claims or specification refer to "a" or "an" element, such reference is not be construed that there is only one of that element.

It is to be understood that where the specification states that a component, feature, structure, or characteristic "may", "might", "can" or "could" be included, that particular component, feature, structure, or characteristic is not required to be included.

Where applicable, although state diagrams, flow diagrams or both may be used to describe embodiments, the invention is not limited to those diagrams or to the corresponding descriptions. For example, flow need not move through each illustrated box or stare, or in exactly the same order as illustrated and described.

Methods of the present invention may be implemented by performing or completing manually, automatically, or a combination thereof, selected steps or tasks.

The descriptions, examples, methods and materials presented in the claims and the specification are not to be construed as limiting but rather as illustrative only.

Meanings of technical and scientific terms used herein are to be commonly understood as by one of ordinary skill in the art to which the invention belongs, unless otherwise defined.

The present invention may be implemented in the testing or practice with methods and materials equivalent or similar to those described herein.

While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has thus far been described, but by the appended claims and their legal equivalents.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

The invention claimed is:

1. A method for generating a three-dimensional (3D) imaging of an object using an electromagnetic transducer array surrounding the object said electromagnetic transducer array comprising:
   a plurality of electromagnetic transducers;
   a transmitter;
   a receiver; and
   a Radio Frequency Signals Measurement Analyzer (RFSMA);
   the method comprising:
   applying RF (radio-frequency) signals to said electromagnetic transducer array using said transmitter;
   receiving, by said receiver, a plurality of RF signals affected by said object from said electromagnetic transducers array;
   receiving and measuring said plurality of affected RF signals using said RFSMA to provide RF data of the object;
   processing said RF data using at least one processor to identify the dielectric properties of said object;

constructing a 3D image of said object; and
providing a two-dimensional (2D) or 3D image of the object using a visual camera.

2. The methods according to claim 1, further comprising:
producing a model of the object, said model comprises a representation of the external and internal shape or parameters of the object.

3. The method of claim 2, wherein said parameters comprise dielectric properties of the object.

4. The method according to claim 1, comprising:
measuring the object from a plurality of bi-static angles using the electromagnetic transducer array.

5. The method according to claim 1, wherein said plurality of electromagnetic transducers are RF antennas.

6. The method according to claim 1, wherein said wideband electromagnetic transducer array is a MIMO (Multiple Input Multiple Output) antenna array.

7. The method according to claim 6, wherein said antenna array is attached to said housing surface.

8. The method of claim 1, comprising a housing having a cavity therein wherein said cavity is configured to contain said object.

9. The method according to claim 8, wherein said housing shape is selected from the group consisting of: a sphere, a cube, a cage.

10. The method according to claim 8, comprising motors and wherein the method further comprising:
rotating the housing or the antenna array or the object with respect to Y or X axis.

11. The method according to claim 8, wherein said housing comprises at least one arc for holding said RF antennas.

12. The method according to claim 11, comprising:
sliding up or down said RF antennas along said at least one arc.

13. The method according to claim 11, comprising:
sliding up or down said RF antennas along said at least one arc while the housing is rotated.

14. The method according to claim 8, comprising:
rotating said object while the housing is in a static position.

15. The method according to claim 1, comprising:
superposing the 2D or 3D images of the object with the 3D image of said object.

* * * * *